(12) United States Patent
Marshall-Jones et al.

(10) Patent No.: US 8,206,690 B2
(45) Date of Patent: Jun. 26, 2012

(54) ORAL HEALTH COMPOSITION

(75) Inventors: Zoe Marshall-Jones, Leicestershire (GB); Marie-Louise Baillon, Leicestershire (GB); Catherine Buckley, Leicestershire (GB)

(73) Assignee: Mars Incorporated, McLean, VA (US)

( * ) Notice: Subject to any disclaimer, the term of this patent is extended or adjusted under 35 U.S.C. 154(b) by 134 days.

(21) Appl. No.: 12/516,294

(22) PCT Filed: Nov. 11, 2007

(86) PCT No.: PCT/GB2007/004526
§ 371 (c)(1),
(2), (4) Date: May 26, 2009

(87) PCT Pub. No.: WO2008/065377
PCT Pub. Date: Jun. 5, 2008

(65) Prior Publication Data
US 2010/0098643 A1    Apr. 22, 2010

(30) Foreign Application Priority Data
Nov. 27, 2006   (GB) .................................. 0623618.6

(51) Int. Cl.
*A61K 36/00*  (2006.01)
*A61K 8/97*   (2006.01)

(52) U.S. Cl. ........................... 424/58; 424/725; 426/805
(58) Field of Classification Search .................. None
See application file for complete search history.

(56) References Cited

U.S. PATENT DOCUMENTS

| | | | |
|---|---|---|---|
| 1,466,578 A | | 8/1923 | Clifton |
| 4,060,602 A | | 11/1977 | Haas et al. |
| 5,612,039 A | * | 3/1997 | Policappelli et al. ......... 424/729 |
| 2004/0202731 A1 | * | 10/2004 | Gow et al. ..................... 424/728 |
| 2006/0134025 A1 | * | 6/2006 | Trivedi et al. .................. 424/58 |
| 2006/0251590 A1 | | 11/2006 | Redmond et al. |

FOREIGN PATENT DOCUMENTS

| | | |
|---|---|---|
| EP | 0321180 A1 | 6/1989 |
| WO | WO 0115680 A1 * | 3/2001 |
| WO | 2008010188 A2 | 1/2008 |

OTHER PUBLICATIONS

Van Dyke et al, Inhibition of gingivitis by topical application of ebselen and rosmarinic acid, Agents and Actions, vol. 19, 5/6, 1986.*
Takeda et al, Orthosiphol D and E, minor diterpenes from Orthosiphon stamineus, Phytochemistry, May 1993. vol. 33, No. 2. p. 411-415.*
International Search Report issued Feb. 21, 2008 (published Jun. 5, 2008) during the prosecution of International Application No. PCT/GB2007/004526.
Written Opinion issued Feb. 21, 2008 (published May 27, 2009) during the prosecution of International Application No. PCT/GB2007/004526.
Internation Preliminary Report on Patentability issued Jun. 3, 2009 (published Jun. 3, 2009) during the prosecution of International Application No. PCT/GB2007/004526.
"*Myrtus communis* L.," Plants Profile, located on website of United States Department of Agriculture, Natural Resources Conservation Service at http://plants.usda.gov/java/profile?symbol=MYCO9&mapType=Large&format=Print&photoID=myco9_001_ahp.jpg, downloaded on Jun. 17, 2011.
"*Orthosiphon* Benth.," Plants Profile, located on website of United States Department of Agriculture, Natural Resources Conservation Service at http://plants.usda.gov/java/profile?symbol=ORTHO7&mapType=Large&format=Print&photoID=ortho7_001_avp.tif, downloaded on Jun. 17, 2011.
Ahamed Basheer et al., "Medicinal potentials of Orthosiphon stamineus Benth.," *WebmedCentral CANCER*, 1(12):WMC001361, 2010.

\* cited by examiner

*Primary Examiner* — Qiuwen Mi
(74) *Attorney, Agent, or Firm* — Fulbright & Jaworski L.L.P.

(57) ABSTRACT

The present invention relates to *Orthosiphon spicatus* for use in oral health applications, an oral composition comprising *Orthosiphon spicatus*, and the use of *Orthosiphon spicatus* or the composition, in the improvement or maintenance of oral health in an animal, preferably through the reduction or control of dental plaque and/or alteration of the bacterial content of dental plaque, in the oral cavity of the animal. The invention also includes *Orthosiphon spicatus* for use in the prevention or treatment of gingivitis in an animal. The invention also provides a method for improving or maintaining oral health in an animal.

7 Claims, 1 Drawing Sheet

ORAL HEALTH COMPOSITION

CROSS-REFERENCE TO RELATED APPLICATIONS

This application is a national filing of PCT/GB2007/004526 filed Nov. 27, 2007 which claims priority from Application 0623618.6 filed on Nov. 27, 2006 in the United Kingdom.

TECHNICAL FIELD

The present invention relates to *Orthosiphon spicatus* for use in oral health applications, an oral composition comprising *Orthosiphon spicatus*, and the use of *Orthosiphon spicatus* or the composition, in the improvement or maintenance of oral health in an animal, preferably through the reduction or control of dental plaque and/or alteration of the bacterial content of dental plaque, in the oral cavity of the animal. The invention also includes *Orthosiphon spicatus* for use in the prevention or treatment of gingivitis in an animal. The invention also provides a method for improving or maintaining oral health in an animal.

BACKGROUND OF THE INVENTION

The need to maintain or improve oral health in an animal is of great importance. Poor oral health can lead to gum disease (gingivitis) and ultimately tooth loss, which can have severe effects on the wellbeing of the animal.

Poor oral health can be caused by a number of diseases and conditions. One of the most prevalent amongst cats and dogs is periodontal disease. Periodontal disease affects all cats and dogs at some stage during their lives. The aetiological agent in all cases of periodontal disease is plaque.

Current dietary methods for reducing or controlling plaque formation (and therefore associated conditions, such as gingivitis), in companion animals are usually mechanical means, such as hard chews or treats which act to scrape the plaque from the teeth, when chewed or consumed by the animal. The mechanical means rely on texture for their efficacy and a chewy rather than brittle texture is preferable to resist breakage of the means and therefore to also increase tooth cleaning time during chewing. Cats are less keen than dogs to chew for prolonged periods. Therefore products for various animals differ in texture to allow for these different preferences.

Textured toys may also be employed, to remove plaque mechanically from the surface of the teeth, without the animal ingesting any of the product that provides the textured surface.

However, the removal of plaque by mechanical means such as textured foodstuffs or toys relies upon the animal spending sufficient time chewing the mechanical means to scrape the plaque from the surface of the teeth. The amount of time required is difficult to assess and to monitor. In addition, plaque control on all tooth surfaces in the oral cavity is difficult to achieve via mechanical abrasion alone and certain teeth receive more efficient cleaning than others.

Plaque may also be removed or reduced by cleaning the teeth by brushing. However, owner compliance with toothbrushing is poor, with the result that very few dogs and cats receive a daily oral care regime of toothbrushing.

As an alternative to mechanical means for the removal of plaque, certain synthetic compounds such as chlorhexidine and triclosan can be used as antibacterial agents to reduce plaque. However, these compounds are broad spectrum antibacterial agents and, as such, may cause an imbalance in healthy gut microflora populations when ingested regularly. In addition, certain plaque bacteria have been associated with periodontal health and treatment with broad spectrum antibacterials would potentially kill these populations and would actually result in a less healthy oral microflora, leading to a reduction in oral health.

Accumulation of bacterial biofilms on the surface of a tooth can lead to gingivitis if not sufficiently addressed. Gingivitis is an inflammation of the gums caused by bacterial plaque that accumulates on the gum line. It can cause soreness, redness and bleeding of the gums.

An additional contributory factor to poor oral health is calculus. Since calculus cannot be removed by toothbrushing in normal cases, it accumulates on the tooth surface and irritates the gum tissue, giving rise to gingivitis. This is a further indication of poor or deteriorating oral health.

The addition of calculus formation inhibitors such as sodium tripolyphosphate to pet foodstuffs or to human oral care products helps to prevent calculus accumulation. However, this does not address the bacterial community composition within the dental plaque that is contributing to the detrimental effects of periodontal disease on the oral health of the animal.

Therefore, there is a need for reducing the effects of dental plaque in an animal, in particular by natural methods, without relying solely on mechanical means or synthetic chemicals or compounds and without stressing the animal. Furthermore, there remains a need for the prevention and treatment of gingivitis in an animal.

BRIEF SUMMARY OF THE INVENTION

Accordingly, the present invention provides *Orthosiphon spicatus* for use in improving or maintaining oral health in an animal.

*Orthosiphon spicatus* is a flowering plant in the family Lamiaceae.

The inventors have unexpectedly found that *Orthosiphon spicatus* is able to improve and/or maintain oral health in an animal.

Preferably, the *Orthosiphon spicatus* improves or maintains the oral health of the animal by controlling or reducing dental plaque in the animal, by which it is meant that disease causing factors produced by the plaque and/or dental plaque is reduced in the oral cavity of the animal.

Dental plaque is a mixed microbial community consisting of aerobic and anaerobic bacteria. Although plaque may vary between individuals the formation process can be broken down into three key events of (i) primary colonisation (adhesion); (ii) secondary colonisation (coaggregation); and (iii) maturation (virulence).

Plaque development begins with a tooth surface covered with a film of proteins and glycoproteins called the tooth salivary pellicle. Pioneer bacterial species adhere to molecules within the salivary pellicle, first forming a monolayer and subsequently pallisades of bacteria perpendicular to the tooth surface.

The microbe is held for a brief period by a weakly attractive force, during which time a number of specific adhesion mechanisms hold the cell close to the surface for a significant time period. These specific interactions may be a combination of lectin-like, electrostatic and hydrophobic interactions that in some instances could involve delicate structures called fibrils or fimbriae that project from the cell surface. Following this, initial attachment is rendered effectively irreversible by the production of extra-cellular polymers.

In humans streptococci are the most common primary colonisers making up between 47-52% of all bacteria adhering to the salivary pellicle.

During and after this initial phase, secondary colonisation by a variety of bacteria occurs leading to a large increase in bacterial diversity. Foremost among the events of secondary colonisation is the process of coaggregation whereby the primary colonisers now act as the substrate for colonisation.

Coaggregation has been described as 'the recognition between surface molecules on two different bacterial cell types so that a mixed cell aggregate is formed'. It has also be described as 'the adherence among partner cells in a suspension'.

Coaggregation is a highly specific process that takes place between specific bacterial 'partners'. Each strain has its own set of partners and mechanisms of cell-cell recognition. Groups of strains also exist which are able to coaggregate with several other strains. Based on human studies, one such organism that dominates these later colonisers is *Fusobacterium nucleatum*, which is a dominant organism in mature dental plaque.

Coaggregation is known to play an important role in human plaque formation. Coaggregation between different strains of canine oral bacteria has been determined in vitro suggesting a similar role for this behaviour in dental plaque formation and development in other animals.

At some point during the development of the plaque biofilm, the rate of change in the overall composition slows. The point at which this happens is currently unknown, although it is thought to take several days for the biofilm to reach this state.

In human plaque, a succession of bacterial species occurs as Gram-positive cocci and rods are progressively replaced by Gram-negative filamentous and flagellated organisms. The maturing biofilm also tends to become increasingly anaerobic as it increases in depth.

It is at this point that the biofilm can be said to have reached a climax community, where a number of the bacteria are reliant on others within the biofilm for their survival. It is during this phase that many organisms associated with periodontal disease are present. These bacteria produce a number of compounds that are the causative factor of periodontal disease, such as proteases and haemolysins. Proteases, in particular trypsin, are reported to have a host of abilities, including the ability to degrade immunoglobulins, inactivate cytokines and their receptors, degrade host tissues and promote bleeding in the oral cavity. The bacteria of the plaque is known as the plaque biomass.

Pathogenic bacteria, such as *Peptostreptococcus* are often present in dental plaque, as well as black pigmenting anaerobes such as *Porphyromonas*, *Bacteroides* and *Prevotella*, all of which are thought to contribute to disease states.

The *Orthosiphon spicatus* of the invention is useful for inhibiting the formation of such biofilms and/or inhibiting the detrimental activities of the biofilm and therefore improving or maintaining oral health by controlling or reducing dental plaque in an animal. The *Orthosiphon spicatus* of the invention is also provided for the prevention or treatment of gingivitis in an animal.

By reducing the level of pathogenic bacteria in the biofilm, the health of the dental plaque is improved. Thus, the *Orthosiphon spicatus* of the invention is useful in altering the bacterial content of the plaque, preferably by reducing the pathogenic bacterial content of the plaque in the oral cavity of an animal. The *Orthosiphon spicatus* may also promote the healthy bacteria of the plaque. The *Orthosiphon spicatus* of the invention is useful in improving the health of the dental plaque present in the oral cavity of an animal.

The *Orthosiphon spicatus* of the invention preferably reduces or inhibits the level of inflammatory proteases and/or black pigmenting anaerobes in dental plaque in an animal. These are key disease causing agents that are found in dental plaque.

Most preferably, *Orthosiphon spicatus* inhibits or reduces pathogenic bacteria in dental plaque, which may include *Peptostreptococcus* sp.

The *Orthosiphon spicatus* of the invention is suitable for any animal including a human. However, in a preferred embodiment the animal is a companion animal or a human. By companion animal it is meant any animal that is kept as a pet, which includes a cat, a dog, a horse, a rabbit, or a guinea pig. Preferably, the composition is for a cat or a dog or a human.

The skilled person understands that other names are used to refer to *Orthosiphon spicatus* including *Orthosiphon stamineus* and *Orthosiphon aristatus*. Other homotypic and heterotypic synonyms include *Clerodendranthus stamineus*, *Orthosiphon aristatus* var. *aristatus*, *Trichostema spirale*, *Clerodendrum spicatum* Thunb, *Ocimum grandiflorum* Blume, *Orthosiphon stamineus* Benth., *Orthosiphon grandiflorus* Bold, *Orthosiphon spiralis*, *Clerodendranthus stamineus* (Benth.), *Orthosiphon velteri* *Orthosiphon spicatus* (Thunb.), *Orthosiphon tagawae* Murata, *Clerodendranthus spicatus* (Thunb.), and it is commonly known as cat's whiskers, java tea or jarva tea.

The *Orthosiphon spicatus* of the invention can be the whole plant or a part thereof. It may be the root, bark, stem, leaf or any combination thereof. The *Orthosiphon spicatus* may be dried, crushed, ground or shredded. Preferably, the *Orthosiphon spicatus* is *Orthosiphon spicatus* leaf.

Additionally or alternatively an extract of *Orthosiphon spicatus* may be used. Suitable extracts include a methanol extract, ethanol extract, a chloroform extract or a water extract.

A second aspect of the invention provides an oral composition comprising *Orthosiphon spicatus*.

The *Orthosiphon spicatus* may comprise between 0.1%-20% by weight of the composition, more preferably 1-15% by weight, more preferably 3-10% by weight, or 1, 2, 3, 4, 5, 6, 7, 8, 9, or 10% by weight. Most preferably, the *Orthosiphon spicatus* comprises about 3% by weight of the composition.

The composition may comprise *Orthosiphon spicatus* as the only active ingredient with respect to the improvement or maintenance of oral health. Alternatively, the composition may comprise *Orthosiphon spicatus* as part of a cocktail including one or more further oral health improving or maintaining, or plaque reducing or controlling components.

Hereinafter in this text, the term "oral composition" covers all compositions that come into contact with the oral cavity, preferably the surface of a tooth of an animal, including a foodstuff, diet and supplement. Any of these forms may be solid, semi-solid or liquid. The composition may be a paste or a gel.

The composition may be in the form of a supplement to be added to any foodstuff that does not contain sufficient levels of *Orthosiphon spicatus* to improve or maintain oral health including prevention or treatment of gingivitis, or to control or reduce dental plaque in an animal, by way of reduction or inhibition of disease causing factors and/or biomass in the plaque.

The concentration of *Orthosiphon spicatus* in the supplement may be used in addition to the animal's main diet or foodstuff. This can be done by including a quantity of the supplement with the animal's diet or by additionally feeding the animal a quantity of the supplement. The supplement can be formed as a foodstuff with extremely high levels of the *Orthosiphon spicatus* composition of the invention, which requires dilution before feeding to the animal. The supplement may be in any form, including solid (e.g. a powder), semi-solid (e.g. a food-like consistency/gel), a liquid, a paste or alternatively, it may be in the form of a tablet or capsule. The liquid can conveniently be mixed in with the food or fed directly to the animal, for example via a spoon or via a pipette-like device. The supplement may be high in one or more components of the invention or may be in the form of a combined pack of at least two parts, each part containing the required level of one or more component.

Preferably the *Orthosiphon spicatus* or a composition comprising *Orthosiphon spicatus* is incorporated into a commercial petfood product composition or a commercial dietary supplement composition. The petfood product may be a dry, semi-dry, a moist or a liquid (drink) product. Moist products include food which is sold in tins or foil containers and has a moisture content of 70 to 90%. Dry products include food which have a similar composition, but with 5 to 15% moisture and presented as biscuit-like kibbles. When the composition comprises a diet, foodstuff or supplement, it is preferably packaged. In this way the consumer is able to identify, from the packaging, the ingredients in the food and identify that it is suitable for the animal in question. The packaging may be metal (usually in the form of a tin or flexifoil), plastic, paper or card. The amount of moisture in any product may influence the type of packaging which can be used or is required.

The composition according to the present invention encompasses any product which an animal may consume in its diet. Thus, the invention covers standard food products for humans or other animals, as well as pet food snacks (for example snack bars, biscuits and sweet products). The composition may be a cooked product. It may incorporate meat or animal derived material (such as beef, chicken, turkey, lamb, blood plasma, marrowbone etc, or two or more thereof). The composition alternatively may be meat free (preferably including a meat substitute such as soya, maize gluten or a soya product) in order to provide a protein source. The composition may contain additional protein sources such as soya protein concentrate, milk proteins, gluten etc. The composition may also contain a starch source such as one or more grains (e.g. wheat, corn, rice, oats, barely etc) or may be starch free. A typical dry commercial dog and cat food contains about 30% crude protein, about 10-20% fat and the remainder being carbohydrate, including dietary fibre and ash. A typical wet, or moist product contains (on a dry matter basis) about 40% fat, 50% protein and the remainder being fibre and ash. The composition of the present invention is particularly relevant for a foodstuff as herein described which is sold as a diet, foodstuff or supplement for a cat, a dog or any other companion animal or a human.

In the present text the terms "domestic" dog and "domestic" cat mean dogs and cats, in particular *Felis domesticus* and *Canis domesticus*.

The composition may be applied to or incorporated within a chew or treat which the animal may consume in addition to a main meal foodstuff. The composition may be provided as a coating on or incorporated within a main meal foodstuff.

Alternatively, the composition may be a liquid, gel, paste or the like which may be applied as a coating to a non-consumable product, such as a toy for an animal. The composition may be incorporated within the product. When the animal chews the toy, the composition comes into contact with some or all of the oral cavity of the animal and improves or maintains the oral health of the animal.

When the composition is incorporated within or coated onto a chewy or hard product, the additional benefit of improving or maintaining the oral health of the animal by removing plaque through the mechanical action of the product against the teeth of the animal is achieved, as well as by the action of the *Orthosiphon spicatus* in the composition.

The inhibition of certain plaque biofilm forming bacteria by *Orthosiphon spicatus* results in the control or reduction of dental plaque in an animal by the reduction of the bacterial content of the dental plaque.

The composition may be used for an animal with any level of oral health in order to improve or maintain oral health in the animal.

The composition may be used for an animal with good or acceptable oral health in order to maintain oral health. The composition in this case may control dental plaque formation and minimise the destructive effects of certain plaque bacteria on the periodontal health of the animal.

Alternatively, the composition may be used for an animal with poor oral health in order to improve the oral health of the animal. The improvement of oral health may be by way of the control of the further accumulation of dental plaque and slow the progression of the disease into the severest stages. It may also reduce dental plaque already present on the surface of the teeth of the animal. In cases of moderate to severe periodontal disease, the animal may require veterinary and/or dental attention prior to using the composition in order to achieve oral health benefits and reduce the frequency of future veterinary and/or dental intervention.

The composition is an oral composition. By oral composition it is meant that during use the oral cavity of the animal is exposed to the composition, and preferably the composition has direct contact with the surface of a tooth of the animal. Most preferably, the surface of a tooth is directly contacted with the *Orthosiphon spicatus* of the composition.

Such an oral composition can include toothpaste, mouthwash or any other such gel, liquid or paste. The oral composition may be a foodstuff, as previously defined.

A third aspect of the invention provides the use of *Orthosiphon spicatus* in the manufacture of a composition for the improvement or maintenance of oral health in an animal. Preferably, the oral health is improved or maintained by the control or reduction of dental plaque in the animal including reduction and/or inhibition of disease causing factors, biomass or pathogenic bacteria. The use of *Orthosiphon spicatus* in the manufacture of a composition for the prevention or treatment of gingivitis is also provided.

The invention, as a fourth aspect, also provides a method for the improvement or maintenance of oral health in an animal comprising administering to the animal *Orthosiphon spicatus* or a composition of the second aspect. Preferably, the method improves or maintains the oral health of the animal by the reduction or control of dental plaque in the animal, as previously defined.

In the method of the fourth aspect, the oral cavity of the animal is exposed to the composition, by way of consumption of the composition through its inclusion in a foodstuff, or by way of a coating comprising the composition on a toy which the animal chews.

Preferably, the method is for use in an animal susceptible to poor oral health or dental plaque, gingivitis or periodontal disease.

The composition may be administered to an animal with poor oral health to reduce the amount of dental plaque or factors contained therein, and then continued feedings may be carried out to control, reduce or inhibit the formation of further dental plaque or any one or more of the factors contained therein. The animal may require veterinary and/or dental treatment before or during use of the composition to remove calculus deposits in order to see a beneficial effect of the *Orthosiphon spicatus* or the composition.

By poor oral health is meant the presence of a number of indicators of this status including calculus and plaque accumulation, gingivitis, oral malodour, presence of gingival recession and/or periodontal pockets, as will be appreciated by the skilled person.

All features of each aspect of the invention relate to all other aspects mutatis mutandis, as appreciated by the skilled person.

BRIEF DESCRIPTION OF THE DRAWINGS

The invention will now be described with reference to the following non-limiting examples and figures, in which.

DETAILED DESCRIPTION OF THE INVENTION

EXAMPLES

Figure 1:
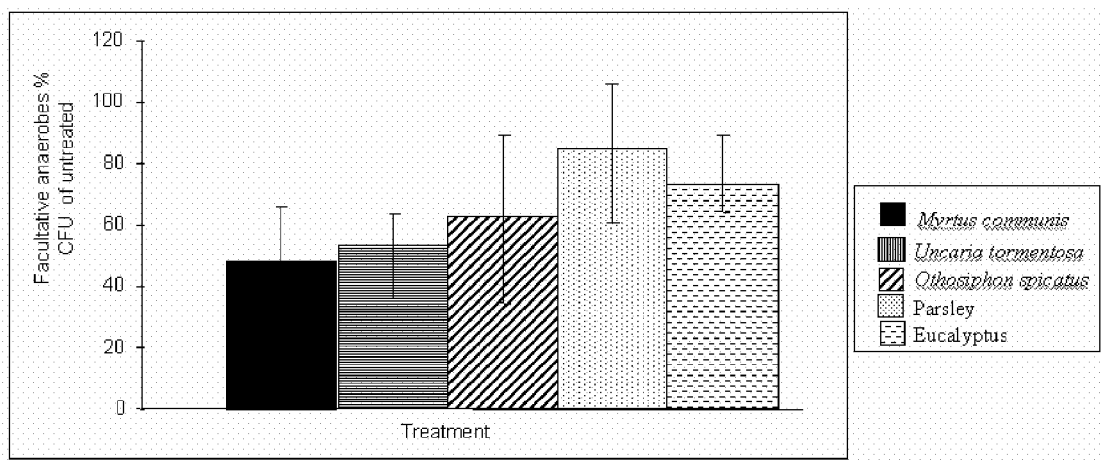
FIG. 1 shows the effect of *Orthosiphon spicatus* on facultative anaerobes cultured from treated biofilms expressed as a percentage of untreated controls. Untreated CFU (100%)=$4.05 \times 10^7$/ml.

*Orthosiphon spicatus* was tested for its ability to control or reduce dental plaque in an animal by way of the following in vitro experiments. Supragingival plaque was obtained from dogs and various assays were carried out, as described below, to determine whether *Orthosiphon spicatus* has the ability to improve or maintain oral health in an animal.

Example 1

Initial assays were set up to help determine whether *Orthosiphon spicatus* would be suitable for use in an animal for improving or maintaining oral health.

These assays included ability to inhibit adhesion of plaque forming bacterial strains and ability to inhibit protease production in such bacterial strains.

*Orthosiphon spicatus* inhibited adhesion of biofilm forming bacterial strains by up to 100% and protease production by up to 21%.

These results indicated that *Orthosiphon spicatus* is able to inhibit undesirable oral bacteria and therefore it was tested in further assays for its ability to improve or maintain oral health.

Example 2

Assay Inoculum

Plaque and Saliva Sampling from Dogs

The assay requires fresh supragingival canine dental plaque and saliva for inoculation. The inoculum consists of pooled dental plaque and unfiltered saliva sampled from a group of 14 dogs, varying in age, breed and oral health status. The plaque and saliva were resuspended in artificial saliva to form the inoculum of approximately 15% plaque and 30% saliva.

Assay Set-Up

The plate biofilm assay (PBA) utilises a 24 well plate format in which biofilms, representative of canine dental plaque, are grown on hydroxyapatite (HA) discs. Prior to being introduced to the 24 well assay plate, each HA disc is preconditioned for 2 hours in a solution of 50% filter sterilised canine saliva in artificial canine saliva. The preconditioning step stimulates the formation of a salivary pellicle on the HA disc surface. Following preconditioning, each HA disc is placed individually into a well on the 24 well plate. The inoculum is divided into two equal aliquots and the active added to one aliquot at the appropriate concentration. The other aliquot represents the control (no active). A 1 ml inoculum is added to each well and the assay plate incubated aerobically with shaking at 38° C. for 48 hours. After 24 hours and 30 hours, the discs are transferred into fresh artificial saliva containing the active at the appropriate concentration as before. Biofilm-covered HA discs are removed from the assay plate for analysis after 48 hours. Each HA disc, with the exception of those being used for biomass quantification, is placed into 500 µl PBS and vortex mixed for 30 seconds to remove biofilm growth from the disc into solution. Biofilm suspensions are then used for analysis. Biofilm-covered HA discs that are being used for biomass quantification are removed from the 24 well assay plate and used directly in the crystal violet assay.

Example 3

*Orthosiphon spicatus* Extracts Tested in the PBA

The extract of *Orthosiphon spicatus* used was a methanol extract (M) for testing in the canine PBA since this showed good activity in the initial screening rounds Extractions were performed as described previously.

In addition, chlorhexidine (Lloyds Pharmacy) was included as the gold standard reference or positive control. However, chlorhexidine is undesirable for use in animal compositions since it is a synthetic chemical and may have potential toxic effects as it is a chemical used in its purest form.

Example 4

Biofilm Measures

The following analyses were used to assess the biofilms produced in the canine PBA and the effects of *Orthosiphon spicatus* and the non-botanical compounds on biofilm development:

Biomass quantification (crystal violet assay)
Protease activity
Bacterial viable counts A brief description of each assay is given below.

Biomass

The total amount of biofilm grown on the HA discs was quantified using the crystal violet staining method. Biomass was represented as being directly proportional to the OD reading at 595 nm ($OD_{595}$) of the samples compared to controls. Results were expressed as the reduction in $OD_{595}$ seen in active-treated samples compared to no active controls, reflecting the effect of the active treatment on the amount of biofilm growth on the disc.

*Orthosiphon spicatus* reduced biomass by 14.6%

Protease Activity

Trypsin-like protease activity was measured using the liquid BAPNA assay, a colourimetric assay in which the amount of trypsin present in a sample is directly proportional to the intensity of the colour developed. Samples were quantified against a trypsin standard curve and results expressed as the percentage inhibition of protease activity in active-treated samples compared to controls.

*Orthosiphon spicatus* reduced protease production by 24.53%.

Bacterial Counts

Viable numbers of bacteria were quantified using Columbia blood agar plates supplemented with haemin and menadione. Aerobes were counted after incubation for 2 days and anaerobes, including black pigmenting colonies (BPC), were counted after incubation at appropriate conditions for 9 days. Plate counts are expressed as colony forming units (cfu) per ml and differences between control and active plates are expressed in logs.

*Orthosiphon spicatus* reduced plate counts of black pigmenting colonies by 2.59 logs, compared to the controls.

Example 5

Statistical Analysis of Data

Each sample was repeated 5 times within the assay. Unless otherwise stated, all extracts were tested in the assay at a concentration of 500 µg/ml. For each sample, all of the values obtained were logged and the means calculated from the log values.

A 2-tailed t-test with unequal variance was then performed. An unequal variance analysis was selected as the individual analyses were independent i.e. the measures were not comparable to one another. For each data set, p values were obtained and these gave an indication of the reproducibility of the data.

Results

A table summarising how *Orthosiphon spicatus* performed in the tests is set out below.

TABLE 1

| Name | Aerobe (log 10 reduction) | Anaerobe (Log 10 reduction) | BPC (Log 10 reduction) | Protease (% reduction) | Biomass (% reduction) |
|---|---|---|---|---|---|
| Chlorhexidine | 2.87 | 2.48 | 2.74 | 95.76 | 94.40 |
| Myrtle | 0.05 | −0.10 | 3.75 | 75.34 | 59.50 |
| Orthosiphon | −0.09 | 0.02 | 2.59 | 24.53 | 14.60 |
| Tepezcohuite | 0.25 | −0.42 | −0.51 | 80.25 | −27.40 |

*Orthosiphon spicatus* significantly reduced black pigmenting colony counts and had a inhibitory effect on protease production and biomass.

Example 6

Testing of Raw Material

The raw plant material of *Orthosiphon spicatus* was also tested in the Plate Biofilm Assay, as well as the extracts described above. The raw plant material was prepared through a 250 µm pore size sieve and was tested at 5000 µg/ml in the assay. The raw material was at least as effective at inhibiting biofilm formation as the previously tested extracts. In fact, the raw material reduced black pigmenting colonies by 3.86 logs, and protease production by 32.65%.

Example 7

Inhibition of Human Plaque

*Orthosiphon spicatus* powder was tested for inhibition of biofilm formation in a human form of the Plate Biofilm Assay. The final concentration of each test agent was 250 µg/ml. Tests were repeated five times in separate assays.

Hydroxyapatite discs were incubated in 20% pooled human saliva for 2 hours at room temperature. An amount of 10 ml of pooled human saliva was collected and combined with plaque inoculum scraped from the tooth surface of human volunteers. The inoculum was added to the 20% pooled saliva at a ratio of 1:3(v/v) and 1.33 ml of the resulting suspension was combined with 2.0 ml artificial saliva (Pratten et al., 1998) and 0.175 ml of the appropriate test agent (*Myrtus communis*, *Uncaria tormentosa*, *Orthosiphon spicatus*, parsley or eucalyptus) at a concentration of 5 mg/ml in sterile water or water (as a negative control to which each test agent was compared). Parsley and eucalyptus were used as positive controls, as they are each well known natural ingredients in oral health products due to their positive effect on oral health.

Triplicate aliquots of each solution (1 ml) were placed in individual wells of a sterile 24 well plate with a single saliva coated hydroxyapatite disc. The discs were incubated for 1 hour at 37° C. in anaerobic conditions (10% $H_2$, 10% $CO_2$, 80% $N_2$), allowing the growth of obligate anaerobes that are found in the sub-gingival recesses associated with periodontitis. This was followed by 24 hours incubation at 37° C. in aerobic conditions.

Biofilms were dispersed, serially diluted and then plated onto CBA (+hemin, menadione) and incubated anaerobically or onto BHY and incubated aerobically. Colonies were counted after 24-48 hours. The results are shown in FIG. 1, where it can be seen that *Orthosiphon spicatus* inhibited the numbers of facultative anaerobic bacteria in human plaque biofilms in vitro compared to untreated (water) control. Surprisingly, *Orthosiphon spicatus* was more effective at reducing levels of these organisms than parsley and eucalyptus, known oral health promotors.

Figure 2:
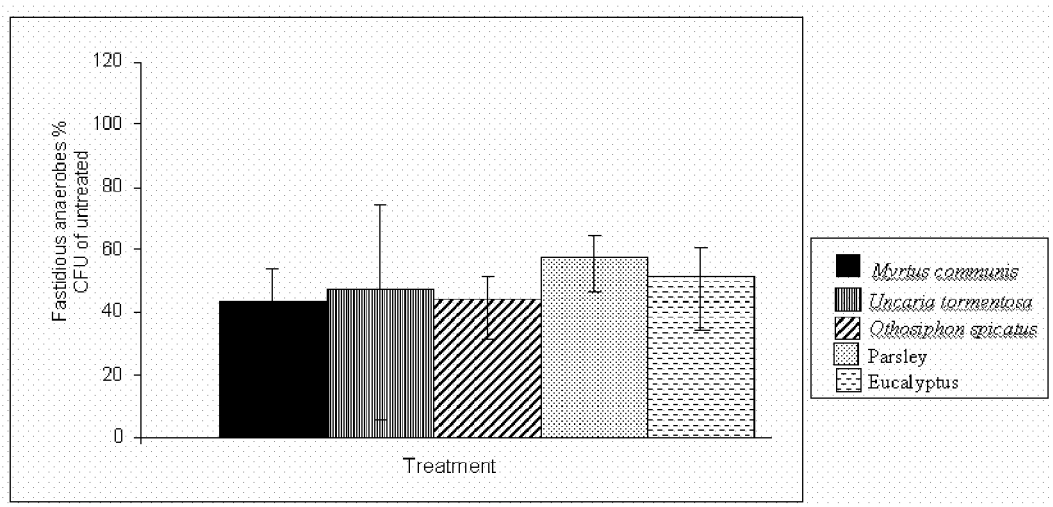
FIG. 2 shows the effect of *Orthosiphon spicatus* on fastidious anaerobes cultured from treated biofilms expressed as a percentage of untreated controls. Untreated CFU (100%)=$2.96 \times 10^7$.

Fastidious anaerobe numbers were also counted, and were also seen to be reduced by *Orthosiphon spicatus* compared to untreated controls, as shown in FIG. 2. It was also unexpectedly found that *Orthosiphon spicatus* performed better than parsley and eucalyptus in inhibiting fastidious anaerobes.

Example 8

Various product applications will require survival of the raw material activity following exposure to temperatures up to 120° C. To test this, the *Orthosiphon spicatus* was heated to autoclaved (120° C. for 10 minutes) and its activity tested in the Plate Biofilm Assay compared with non heat-treated controls.

Heat treatment of *Orthosiphon spicatus*, as described above, does not affect its performance. Heat-treated *Orthosiphon spicatus* reduces biomass by 73.9%, compared to 89.4% in the unheated control. Protease production is inhibited 87.43% and 86.59% by the heat-treated and non-heated material respectively.

What is claimed is:

1. A method of reducing the bacterial content of dental plaque in a dog or cat in need thereof comprising administering to the dog or cat in need thereof an effective amount of *Orthosiphon spicatus* in a pet food composition in order to maintain or improve the oral health of said dog or cat.

2. The method of claim 1, wherein *Orthosiphon spicatus* comprises between 0.1% and 20% of the *Orthosiphon spicatus* pet food composition by weight.

3. The method of claim 2, wherein *Orthosiphon spicatus* comprises about 0.1% to 4% of the *Orthosiphon spicatus* pet food composition by weight.

4. The method of claim 1, wherein the *Orthosiphon spicatus* pet food composition is selected from a group consisting of a dry petfood, a wet petfood, and a treat for a companion animal.

5. The method of claim 1, wherein the *Orthosiphon spicatus* pet food composition comprises 5 to 15% moisture or 70 to 90% moisture.

6. The method of claim 1, further comprising identifying in the dog or cat an indication of the need of the *Orthosiphon spicatus* pet food composition.

7. The method of claim 6, wherein the indication of need is selected from the group consisting of calculus accumulation, plaque accumulation, gingivitis, oral malodour, presence of gingival recession, periodontal pockets and combinations thereof.

* * * * *

UNITED STATES PATENT AND TRADEMARK OFFICE
CERTIFICATE OF CORRECTION

Page 1 of 1

PATENT NO. : 8,206,690 B2
APPLICATION NO. : 12/516294
DATED : June 26, 2012
INVENTOR(S) : Zoe Marshall-Jones et al.

It is certified that error appears in the above-identified patent and that said Letters Patent is hereby corrected as shown below:

ON THE TITLE PAGE:

Item (22) PCT Filed: should read:   Nov. 27, 2007

Signed and Sealed this
Seventh Day of August, 2012

David J. Kappos
*Director of the United States Patent and Trademark Office*